(12) United States Patent
Thomas et al.

(10) Patent No.: US 8,133,266 B2
(45) Date of Patent: Mar. 13, 2012

(54) EXPANDABLE TIP DELIVERY SYSTEM AND METHOD

(75) Inventors: Richard Thomas, Cloverdale, CA (US); Janelle Chang, San Francisco, CA (US); Charles Thomas, Santa Rosa, CA (US); Aidan O'Leary, Santa Rosa, CA (US); David Gray, Windsor, CA (US); Arif Iftekhar, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 739 days.

(21) Appl. No.: 11/734,699

(22) Filed: Apr. 12, 2007

(65) Prior Publication Data

US 2008/0255652 A1 Oct. 16, 2008

(51) Int. Cl.
*A61F 2/84* (2006.01)

(52) U.S. Cl. ...................................... 623/1.11

(58) Field of Classification Search .................. 623/1.15, 623/1.32, 1.11, 1.23; 606/108, 185, 194, 606/200
See application file for complete search history.

(56) References Cited

U.S. PATENT DOCUMENTS

| 5,415,664 | A | * | 5/1995 | Pinchuk | 623/1.11 |
| 5,685,826 | A | * | 11/1997 | Bonutti | 600/204 |
| 7,306,617 | B2 | * | 12/2007 | Majercak | 606/198 |
| 7,473,271 | B2 | * | 1/2009 | Gunderson | 623/1.12 |
| 2004/0087965 | A1 | * | 5/2004 | Levine et al. | 606/108 |
| 2006/0184234 | A1 | * | 8/2006 | Frazier et al. | 623/1.36 |
| 2007/0021778 | A1 | * | 1/2007 | Carly | 606/213 |
| 2008/0255652 | A1 | * | 10/2008 | Thomas et al. | 623/1.11 |

* cited by examiner

*Primary Examiner* — Thomas J Sweet
*Assistant Examiner* — Christopher Schubert (57) ABSTRACT

A method of deploying a stent-graft in a curved vessel includes deploying an expandable tip to center a proximal end of the catheter containing a stent-graft in the curved vessel. A sheath is retracted to expose the stent-graft and the stent-graft self-expands into the curved vessel. By centering the catheter containing the stent-graft prior to deployment with the expandable tip, the accuracy of stent graft placement within the curved vessel is improved.

24 Claims, 7 Drawing Sheets

EXPANDABLE TIP DELIVERY SYSTEM AND METHOD

BACKGROUND OF THE INVENTION

1. Field of the Invention

This invention relates generally to medical devices and procedures, and more particularly to a method and system of deploying stent-grafts in a vascular system.

2. Description of Related Art

Prostheses for implantation in blood vessels or other similar organs of the living body are, in general, well known in the medical art. For example, prosthetic vascular grafts formed of biocompatible materials (e.g., Dacron or expanded, porous polytetrafluoroethylene (PTFE) tubing) have been employed to replace or bypass damaged or occluded natural blood vessels.

A graft material supported by a framework is known as a stent-graft or endoluminal graft. In general, the use of stent-grafts for treatment or isolation of vascular aneurysms and vessel walls which have been thinned or thickened by disease (endoluminal repair or exclusion) is well known.

Many stent-grafts, are "self-expanding", i.e., inserted into the vascular system in a compressed or contracted state, and permitted to expand upon removal of a restraint. Self-expanding stent-grafts typically employ a wire or tube configured (e.g., bent or cut) to provide an outward radial force and employ a suitable elastic material such as stainless steel or Nitinol (nickel-titanium). Nitinol may additionally employ shape memory properties.

The self-expanding stent-graft is typically configured in a tubular shape of a slightly greater diameter than the diameter of the blood vessel in which the stent-graft is intended to be used. In general, stent-grafts are typically deployed through a minimally invasive intraluminal delivery, i.e., cutting through the skin to access a lumen or vasculature or percutaneously via successive dilatation, at a convenient (and less traumatic) entry point, and routing the stent-graft through the lumen to the site where the prosthesis is to be deployed.

Intraluminal deployment in one example is effected using a delivery catheter with coaxial inner tube, it having near its distal end a plunger or stop, and sheath, arranged for relative axial movement. The stent-graft is compressed and disposed within the distal end of the sheath in front of the inner tube stop.

The catheter is then maneuvered, typically routed though a lumen (e.g., vessel), until the end of the catheter (and the stent-graft) is positioned in the vicinity of the intended treatment site. The stop on the inner tube is then held stationary while the sheath of the delivery catheter is withdrawn. The stop prevents the stent-graft from moving back as the sheath is withdrawn.

As the sheath is withdrawn, the stent-graft is gradually exposed from a proximal end to a distal end of the stent-graft, the exposed portion of the stent-graft radially expands so that at least a portion of the expanded portion is in substantially conforming surface contact with a portion of the interior of the lumen, e.g., blood vessel wall.

In straight vessels, placement of the stent-graft is relatively straightforward. However, in complex vessels, e.g., in the aortic arch or other curved vessel, placement of the stent-graft becomes less than ideal.

More particularly, in the aortic arch, the stiffness of the delivery catheter causes the distal tip of the delivery catheter to be positioned closely to the outer radius of curvature of the aortic arch. This positioning of the distal tip of the delivery system combined with the effect of blood flow as the stent-graft is deployed results in a high likelihood for asymmetrical deployment of the stent-graft.

To illustrate, as the stent-graft deployment begins, the blood flow catches the initially deployed springs like the sail of a sail boat and causes some spring and or stent graft portions to bend preferentially in the direction of blood flow to cause uneven deployment such that the portion of the springs or stent graft closer to the inner radius of curvature of the aortic arch bend out from the stent graft and downward when deployed high in the vessel as shown in the example figures. As a result, the proximal end of the stent-graft is not deployed orthogonal to the wall of the aortic arch. To correct the initial asymmetrical deployment, the physician typically repositions the stent-graft, which is generally undesirable depending upon the particular application. Further, due to the repositioning, additional cuff (extender) type stent-grafts may need to be deployed.

The proximal end of the stent-graft is the end closest to the heart whereas the distal end is the end furthest away from the heart as deployed. In contrast and of note, the distal end of the catheter is usually identified to the end that is farthest from the operator (handle) while the proximal end of the catheter is the end nearest the operator (handle). For purposes of clarity of discussion, as used herein, the distal end of the catheter is the end that is farthest from the operator (the end furthest from the handle) while the distal end of the stent-graft is the end nearest the operator (the end nearest the handle), i.e., the distal end of the catheter and the proximal end of the stent-graft are the ends furthest from the handle while the proximal end of the catheter and the distal end of the stent-graft are the ends nearest the handle. However, those of skill in the art will understand that depending upon the access location, the stent-graft and delivery system description may be consistent or opposite in actual usage. When using femoral artery access the distal ends are opposite in the device and catheter, while when using a brachial artery access they are consistent.

SUMMARY OF THE INVENTION

In accordance with one embodiment, a method of deploying a stent-graft in a curved vessel with an expandable tip stent-graft delivery system includes deploying an expandable tip of the expandable tip stent-graft delivery system to center a proximal end of the stent-graft in the curved vessel. A sheath of the expandable tip stent-graft delivery system is retracted to expose the stent-graft, the stent-graft thereby self-expands into the curved vessel. After deployment of the stent-graft, the expandable tip is collapsed and the stent-graft delivery system is removed.

By centering the stent-graft prior to deployment with the expandable tip, the initial deployment of the stent-graft is substantially orthogonal to the axial centerline of the curved vessel at the deployment location. As the initial deployment of the stent-graft is symmetric, repositioning of the stent-graft after initial deployment is avoided. Accordingly, the stent-graft is accurately placed within the curved vessel and the need to deploy additional stent-grafts is avoided.

These and other features will be more readily apparent from the detailed description set forth below taken in conjunction with the accompanying drawings.

BRIEF DESCRIPTION OF THE DRAWINGS

In the following description, the same or similar elements are labeled with the same or similar reference numbers.

DETAILED DESCRIPTION

Figure 5:
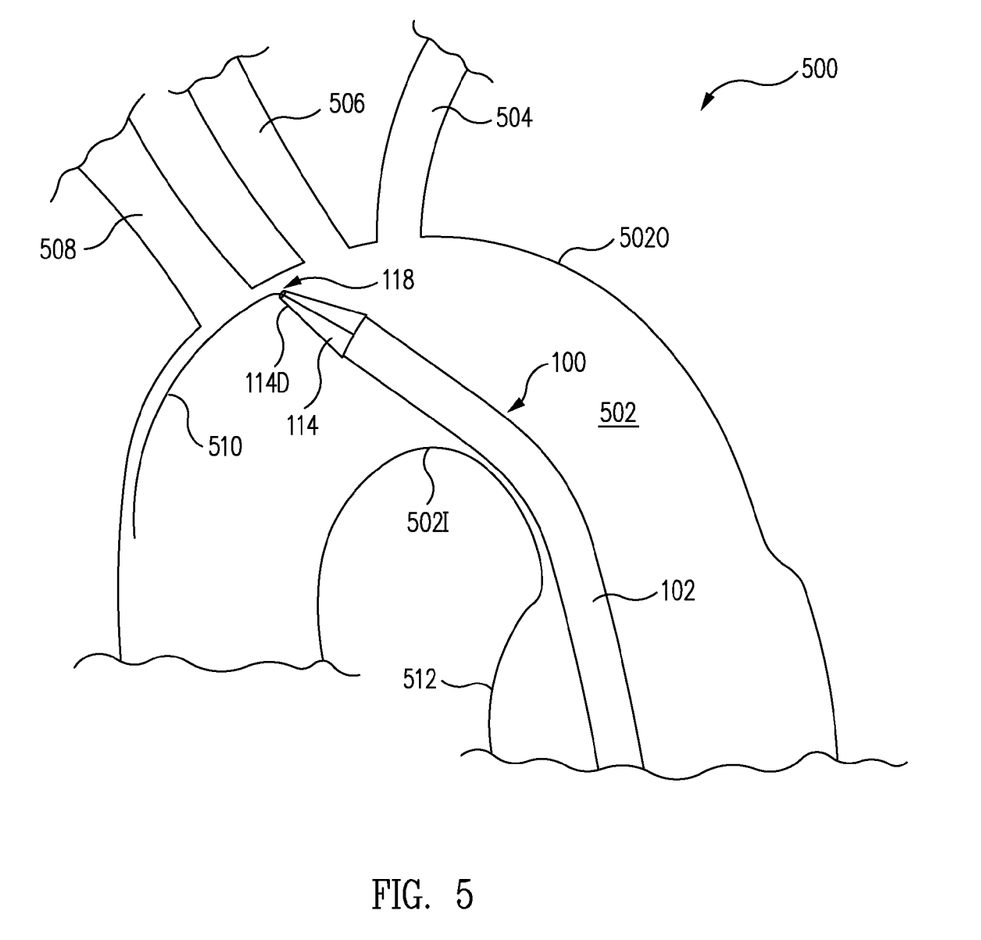
FIG. 5 is a partial cross-sectional view of a vascular system including the expandable tip stent-graft delivery system of FIG. 1 within a curved vessel.
Figure 6:
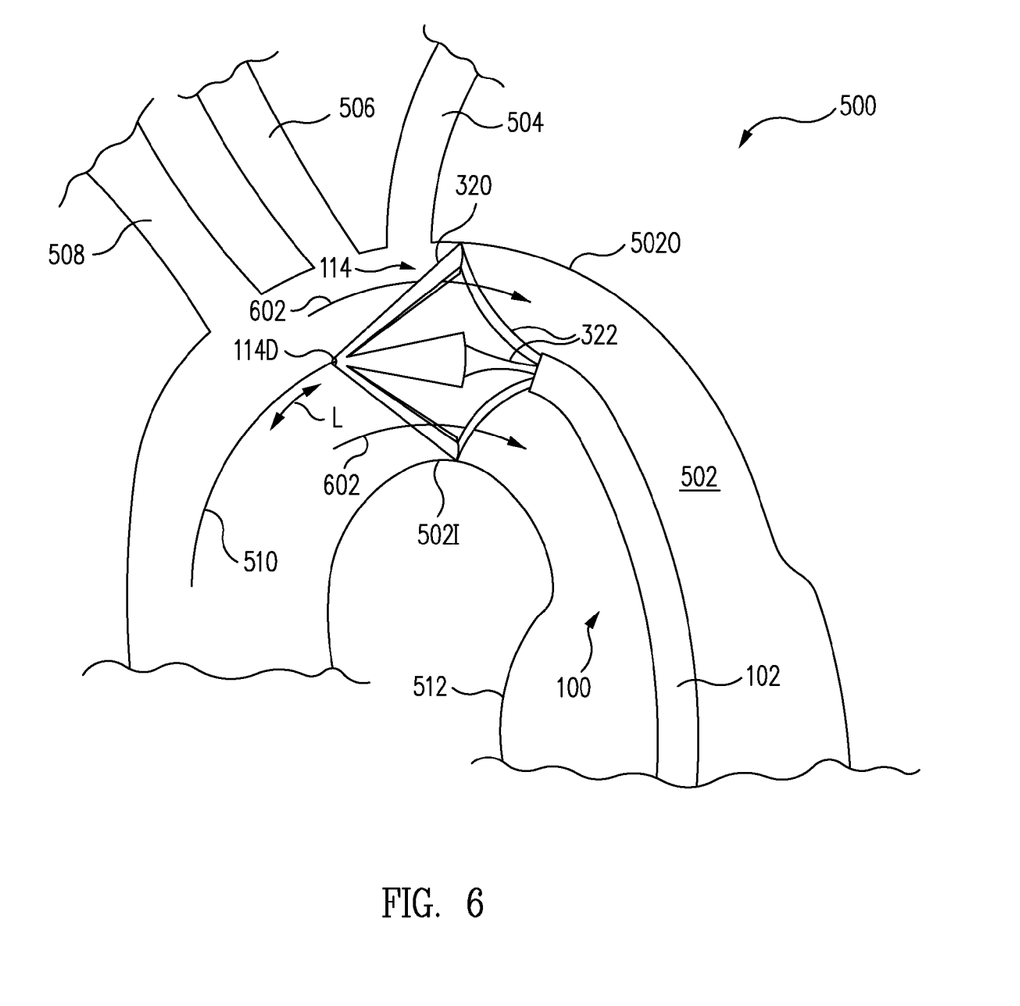
FIG. 6 is a partial cross-sectional view of the vascular system of FIG. 5 after deployment of the expandable tip of the expandable tip stent-graft delivery system.
Figure 7:
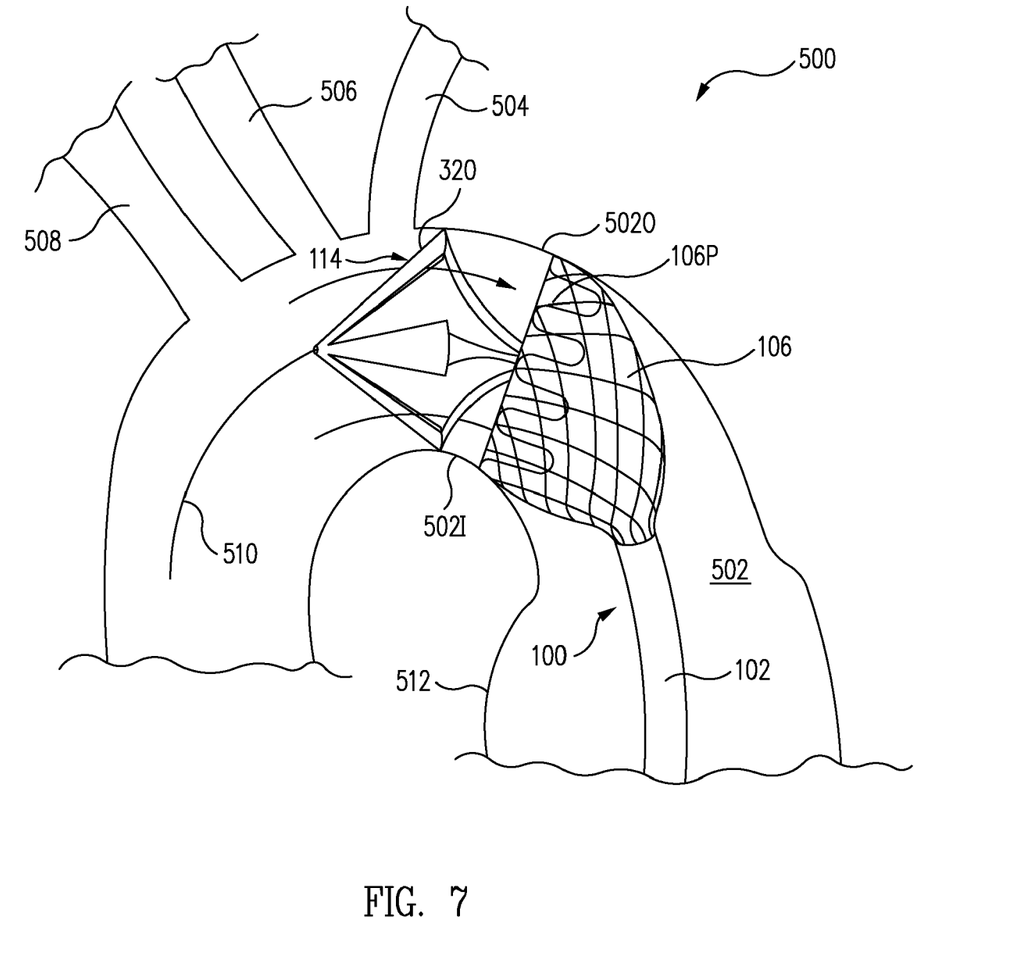
FIG. 7 is a partial cross-sectional view of the vascular system of FIG. 6 after deployment of the expandable tip and partial deployment of a stent-graft of the expandable tip stent-graft delivery system.

In accordance with one embodiment, referring to FIGS. 5, 6, 7, and 8 together, a method of deploying a stent-graft 106 in a curved vessel 502 with an expandable tip stent-graft delivery system 100 includes deploying an expandable tip 114 to center a distal end of the delivery catheter in curved vessel 502 as illustrating FIG. 6. A sheath 102 is retracted to expose stent-graft 106 as illustrated in FIG. 7, wherein stent-graft 106 self-expands into curved vessel 502. After deployment of stent-graft 106, expandable tip 114 is collapsed.

By centering the distal end of the delivery catheter prior to deployment with expandable tip 114, the initial deployment of stent-graft 106 is substantially orthogonal to the central longitudinal axis of the curved vessel 502. As the initial deployment of stent-graft 106 is symmetric, repositioning of stent-graft 106 sometime required when using prior art systems after initial deployment is avoided. Accordingly, there is a high likelihood that the initial placement of stent-graft 106 is accurate within curved vessel 502.

Figure 1:
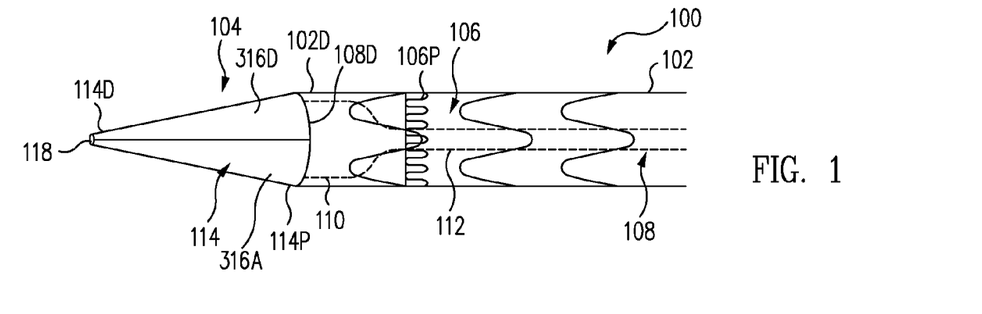
FIG. 1 is a schematic side view of an expandable tip stent-graft delivery system in accordance with one embodiment.

FIG. 1 is a schematic side view of an expandable tip stent-graft delivery system 100 in accordance with one embodiment. Referring now to FIG. 1, expandable tip stent-graft delivery system 100 includes a sheath 102, an expandable tip member 104, a stent-graft 106, and an inner member 108.

Sheath 102 is a hollow tube and defines a lumen therein through which inner member 108 extends. Sheath 102 includes a distal end 102D. Sheath 102 is illustrated as being transparent to allow visualization of features therein. However, in other examples, a sheath similar to sheath 102 is opaque.

Inner member 108 (illustrated by the dashed lines) is also a hollow tube and defines a lumen therein through which runners of expandable tip member 104 extend. Inner member 108 includes a distal end 108D having a cup 110. Cup 110 of inner member 108 has a greater diameter than the remaining proximal portion 112 of inner member 108. Proximal portion 112 extends proximally from cup 110.

As discussed further below, cup 110 is an enclosure into which runners of expandable tip member 104 are advanced and retracted to expand (deploy) and collapse an expandable tip 114 of expandable tip member 104. Further, cup 110 has an outer diameter approximately equal to, but slightly smaller than, the inner diameter of sheath 102 facilitating a snug fit of sheath 102 around cup 110.

Stent-graft 106 is a self-expanding stent-graft and includes a proximal end 106P. Stent-graft 106 includes a graft material supported by a framework. Stent-graft 106 employs a wire or tube configured (e.g., bent or cut) to provide an outward radial force and employs a suitable elastic material such as stainless steel or Nitinol (nickel-titanium). Nitinol may additionally employ shape memory properties. Although a particular illustration of stent-graft 106 is set forth in the figures, it is to be understood that stent-graft 106 may appear differently in actual implementation depending upon the particular type of stent-graft used.

Stent-graft 106 is radially constrained by sheath 102. More particularly, stent-graft 106 exerts an outward radial force on sheath 102. Stent-graft 106 is radially constrained in the annular space between sheath 102 and proximal portion 112 of inner member 108.

Figure 2:
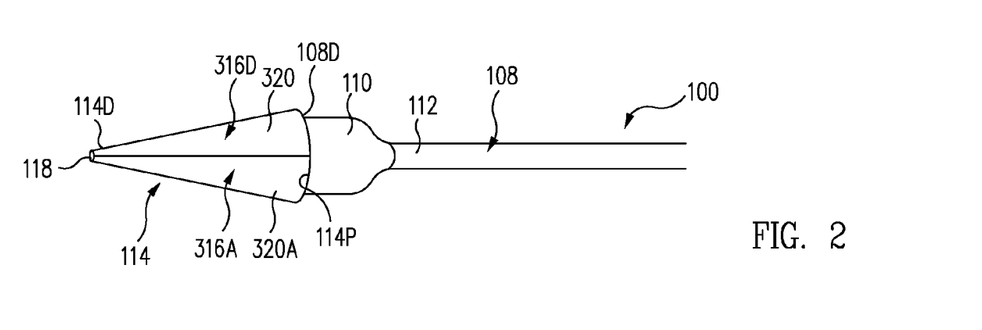
FIGS. 2, 3, 4 are perspective views illustrate the expandable tip stent-graft delivery system of FIG. 1 at various stages during deployment of an expandable tip.
Figure 3:
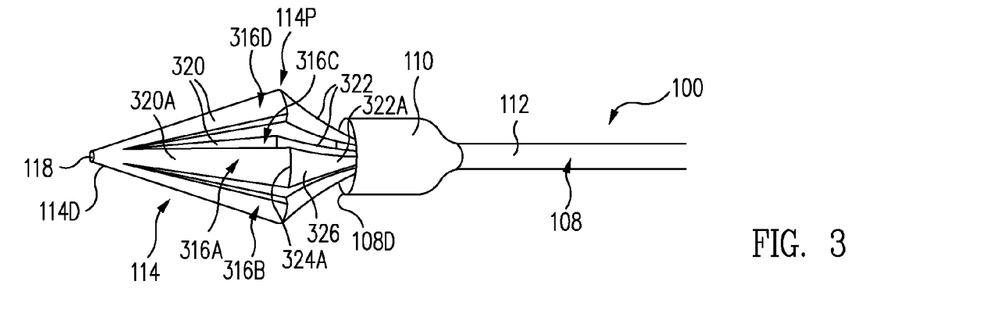
Figure 4:
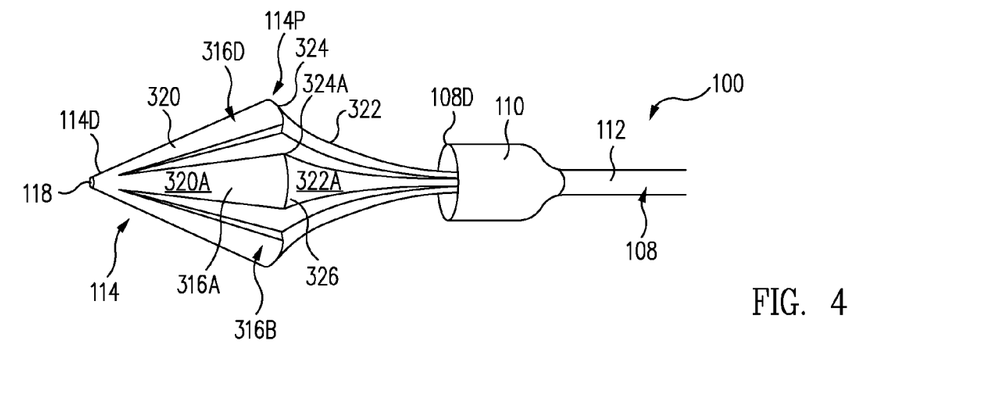

FIGS. 2, 3, 4 are perspective views illustrate expandable tip stent-graft delivery system 100 at various stages during deployment of expandable tip 114. In FIGS. 2, 3, 4, sheath 102 and stent-graft 106 are not illustrated for clarity of presentation although it is to be understood that expandable tip stent-graft delivery system 100 includes sheath 102 and stent-graft 106 at the stages of deployment illustrated in FIGS. 2, 3, and 4.

Referring now to FIGS. 1, 2, 3, and 4 together, expandable tip member 104 includes a plurality of splines 316A, 316B, 316C, 316D, collectively splines 316. In accordance with this example, expandable tip member 104 includes four splines 316 although can have more or less splines in other examples. Illustratively, splines 316 are long narrow strips, e.g., of nitinol, stainless steel, polymer, or other resilient material. In one example, splines 316 are molded, e.g., from polymer.

The distal ends of splines 316 are connected to one another to form a distal end 114D of expandable tip 114. A guide wire opening 118 is formed in distal end 114D of expandable tip 114.

Each spline 316 includes a tip petal 320 and a runner 322 connected to one another at an elbow 324. To illustrate, spline 316A includes a first tip petal 320A of the plurality of tip petals 320, a first runner 322A of the plurality of runners 322, and a first elbow 324A of the plurality of elbows 324. Runner 322A is connected to tip petal 320A by elbow 324A. The other splines 316B, 316C, 316D includes tip petals 320, runners 322 and elbows 324 in a similar fashion.

Tip petals 320, sometimes called wings (or fingers), extend proximally from distal end 114D of expandable tip 114 to elbows 324. Runners 322 extended proximally from elbows 324 to the handle of expandable tip stent-graft delivery system 100 as discussed in greater detail below with reference to FIG. 9.

Tip petals 320 collectively formed expandable tip 114. In its collapsed pre-deployment configuration illustrated in FIG. 2, expandable tip 114 includes a tapered outer surface that gradually increases in diameter. More particularly, the tapered outer surface has a minimum diameter at distal end 114D of expandable tip 114 and gradually increases in diameter proximally, i.e., in the direction of the operator (or handle of expandable tip stent-graft delivery system 100), to have a maximum diameter at elbows 324, which define the proximal end 114P of expandable tip 114. Other tip shapes such as bullet-shaped tips could also be used.

Expandable tip 114 provides trackability in vessels. As set forth above, expandable tip 114 includes guide wire opening 118 therein allowing passage of a guidewire through expandable tip 114.

Each tip petal 320 has a minimum width on the tapered outer surface of expandable tip 114 at distal end 114D of expandable tip 114 and gradually increases in width proximally to have a maximum width at elbows 324.

Conversely, runners 322 have a substantially uniform width along the longitudinal length of runners 322. However, as illustrated in FIG. 3, 4, in accordance with this example, runners 322 have flared ends 326 at the distal end of runners 322 to match the width of tip petals 320 at elbows 324. However, in other examples, runners similar to runners 322 are entirely of a uniform width, i.e., do not have flared ends 326.

Elbows 324 are bends (or hinges) between tip petals 320 and runners 322. Generally, outer corners of elbows 324 are smoothly rounded to prevent the corners of the elbows 324 from digging into and damaging the vessel into which elbows 324 contact as discussed further below.

In accordance with one embodiment, expandable tip 114 is self-expanding as illustrated in FIGS. 2, 3 and 4.

Paying particular attention to FIG. 2, prior to deployment of expandable tip 114, expandable tip 114 is in its collapsed configuration. In its collapsed configuration, tip petals 320 are substantially in contact with one another along the entire length of tip petals 320 and collectively form a continuous tapered outer surface of expandable tip 114. Generally, inner member 108, i.e., cup 110, radially constrains runners 322 and thus the proximal end of expandable tip 114.

Further, in a retracted or collapsed configuration the proximal ends of the expandable tip 114 is seated on distal end 108D of inner member 108. More particularly, the diameter at proximal end 114P of expandable tip 114 is greater than the diameter of cup 110 of inner member 108.

Referring now to FIG. 3, in the initial stages of deployment of expandable tip 114, runners 322 are advanced (moved distally (forward)) out of inner member 108. This causes expandable tip 114 to move distally from inner member 108 thus releasing the radial constraint of inner member 108 on runners 322 at expandable tip 114. As the radial constraint of inner member 108 on runners 322 is released, i.e., as runners 322 are advanced out of inner member 108, expandable tip 114 begins to self-expand.

As expandable tip 114 self-expands, tip petals 320 move radially outwards from one another at proximal end 114P of expandable tip 114. Stated another way, expandable tip 114, sometimes called a flower tip, begins to open such that the outer diameter of proximal end 114P of expandable tip 114 increases.

Referring now to FIG. 4, in the final stage of deployment of expandable tip 114, runners 322 are advanced out of inner member 108 to a length at which inner member 108 releases expandable tip 114, i.e., no longer radially constrains expandable tip 114 to any significant manner. Accordingly, expandable tip 114 is in its relaxed configuration.

When expandable tip 114 is in its relaxed configuration as illustrated FIG. 4, tip petals 320 spread outward from one another proximally from distal end 114D of expandable tip 114 due to the self-expansion of expandable tip 114. More particularly, tip petals 320 are separated from one another, except of course at distal end 114D of tapered tip 114, where tip petals 320 are connected to one another.

Thus, in its relaxed configuration as illustrated in FIG. 4, expandable tip 114 has a greater outer diameter than in its radially contracted state as illustrated in FIG. 2. This expansion of tapered tip 114 is used to center stent-graft 106 (illustrated in FIG. 1) within a vessel prior to deployment of stent-graft 106 as discussed in greater detail below with reference to FIGS. 5, 6, 7, and 8.

Expandable tip 114 is collapsed in the opposite manner as expandable tip 114 is expanded as set forth above. More particularly, runners 322 are retracted (pulled) into inner member 108. This causes runners 322 and thus expandable tip 114 to be radially compressed and collapsed by inner member 108. Illustratively, expandable tip 114 goes from the stage illustrated in FIG. 4 (fully expanded), to the stage illustrated in FIG. 3 (partially expanded) to the stage illustrated in FIG. 2 (fully collapsed).

FIG. 5 is a partial cross-sectional view of a vascular system 500 including expandable tip stent-graft delivery system 100 of FIG. 1 within a curved vessel 502. Curved vessel 502 can be any curved vessel but is illustrated as the aortic arch in accordance with this example. Curved vessel 502 includes an inner radius of curvature 502I and outer radius of curvature 502O.

Branching from curved vessel 502 are three branch vessels 504, 506, and 508, e.g., the left subclavian artery (LSA), the left common carotid artery (LCC), and the brachiocephalic artery. Although three branch vessels 504, 506, and 508 are illustrated, it is to be understood that expandable tip stent-graft delivery system 100 can be used in any vessel, i.e., with or without curves and/or with or without branch vessels.

Initially, a guide wire 510 is guided through curved vessel 502. Expandable tip stent-graft delivery system 100 is advanced over guide wire 510, which enters expandable tip stent-graft delivery system through guide wire opening 118 in expandable tip 114. Due to the inherent stiffness of expandable tip stent-graft delivery system 100, expandable tip stent-graft delivery system 100 conforms to outer radius of curvature 502O. More particularly, distal end 114D of expandable tip 114 presses on or is located adjacent to outer radius of curvature 502O.

FIG. 6 is a partial cross-sectional view of vascular system 500 of FIG. 5 after deployment of expandable tip 114 of expandable tip stent-graft delivery system 100. As illustrated in FIG. 6, expandable tip 114 is deployed as discussed above in reference to FIGS. 2, 3, and 4. More particularly, runners 322 are advanced out of the inner member, facilitating self expansion of expandable tip 114.

Self expansion of expandable tip 114 causes expandable tip 114 and the distal end of the catheter attached thereto to be centered along the longitudinal axis of and within curved vessel 502. More particularly, as tip petals 320 self-expand, one or more of tip petals 320 contact the vessel wall at or near outer radius of curvature 502O of curved vessel 502. This contact and expansion causes distal end 114D of expandable tip 114 to move away from outer radius of curvature 502O of curved vessel 502 and towards inner radius of curvature 502I. Generally, distal end 114D of expandable tip 114 is moved to the center of curved vessel 502, i.e., to be located on or near a longitudinal axis L of curved vessel 502.

Thus, as illustrated FIG. 6, the distal end of the catheter is centered within curved vessel 502.

Further, as illustrated by the arrows 602 in FIG. 6, blood, i.e., fluid, continues to flow through curved vessel 502. More particularly, as expandable tip 114 self expands, tip petals 320 are separated from one another thereby forming openings for passage of blood through expandable tip 114. Also providing a centralized alignment for the end of the catheter.

FIG. 7 is a partial cross-sectional view of vascular system 500 of FIG. 6 after deployment of expandable tip 114 and partial deployment of stent-graft 106 of expandable tip stent-graft delivery system 100. Referring now to FIG. 7, after proximal end 106P of stent-graft 106 is centered within curved vessel 502 by deploying expandable tip 114 as set forth above, sheath 102 is retracted to expose (deploy) stent-graft 106. As stent-graft 106 is exposed, proximal end 106P of stent-graft 106 self expands in curved vessel 502.

By centering catheter containing stent-graft 106 prior to deployment with expandable tip 114, the initial deployment of stent-graft 106 is approximately (substantially) orthogonal to the longitudinal axis of curved vessel 502, i.e., the vessel wall of curved vessel 502. As the initial deployment of stent-graft 106 is symmetric, repositioning of stent-graft 106 as might have been done in prior art devices after initial deployment is avoided. Accordingly, stent-graft 106 is accurately placed within curved vessel 502 and deployment of additional cuff and extension stent-grafts is avoided as might have been done in prior art devices.

Figure 8:
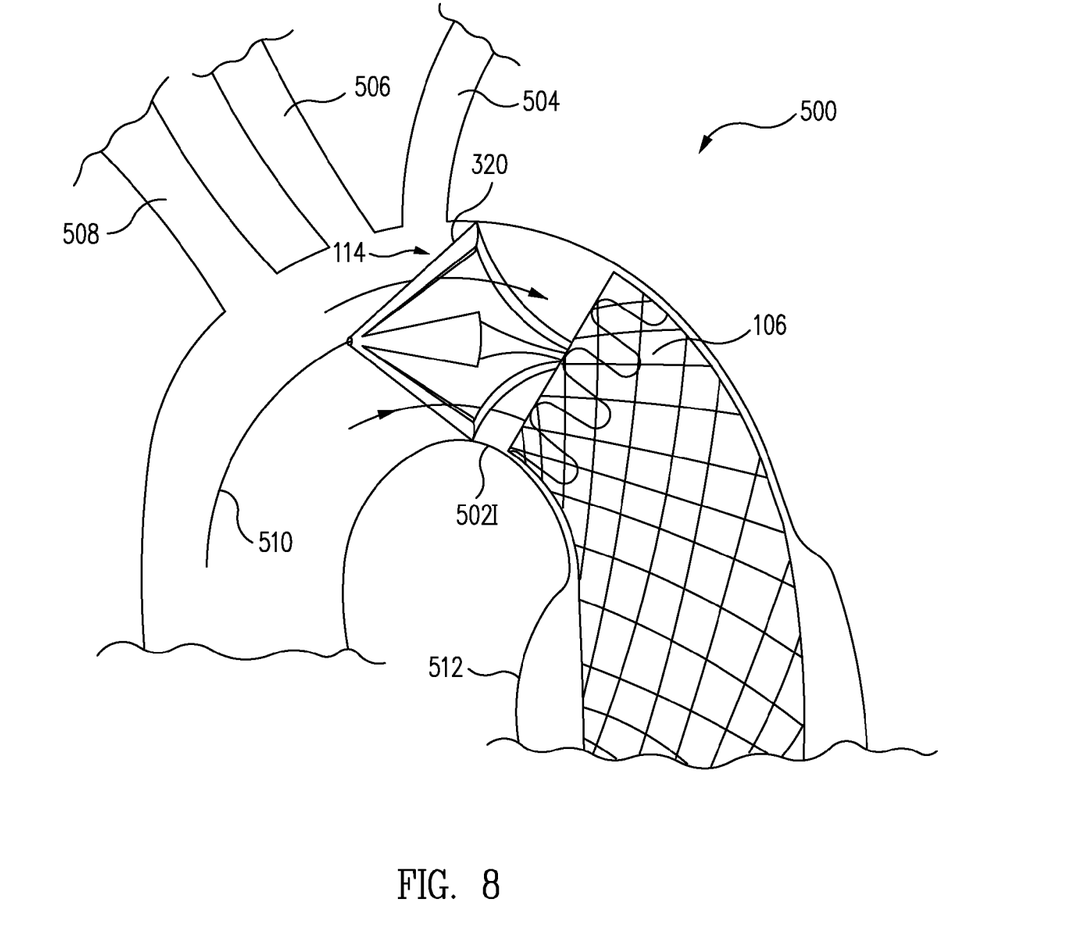
FIG. 8 is a partial cross-sectional view of the vascular system of FIG. 7 after complete deployment of the stent-graft.

FIG. 8 is a partial cross-sectional view of vascular system 500 of FIG. 7 after complete deployment of stent-graft 106 (though only the proximal end of the stent graft 106 is shown). Referring now to FIG. 8, sheath 102 is fully retracted to completely expose stent-graft 106. Accordingly, stent graft 106 is completely deployed. Illustratively, stent-graft 106 acts as a conduit and seal to prevent blood flow to an aneurysm 512 in curved vessel 502.

After deployment of stent-graft 106, expandable tip 114 is collapsed as discussed above, and expandable tip stent-graft delivery system 100 is removed from the patient.

Figure 9:
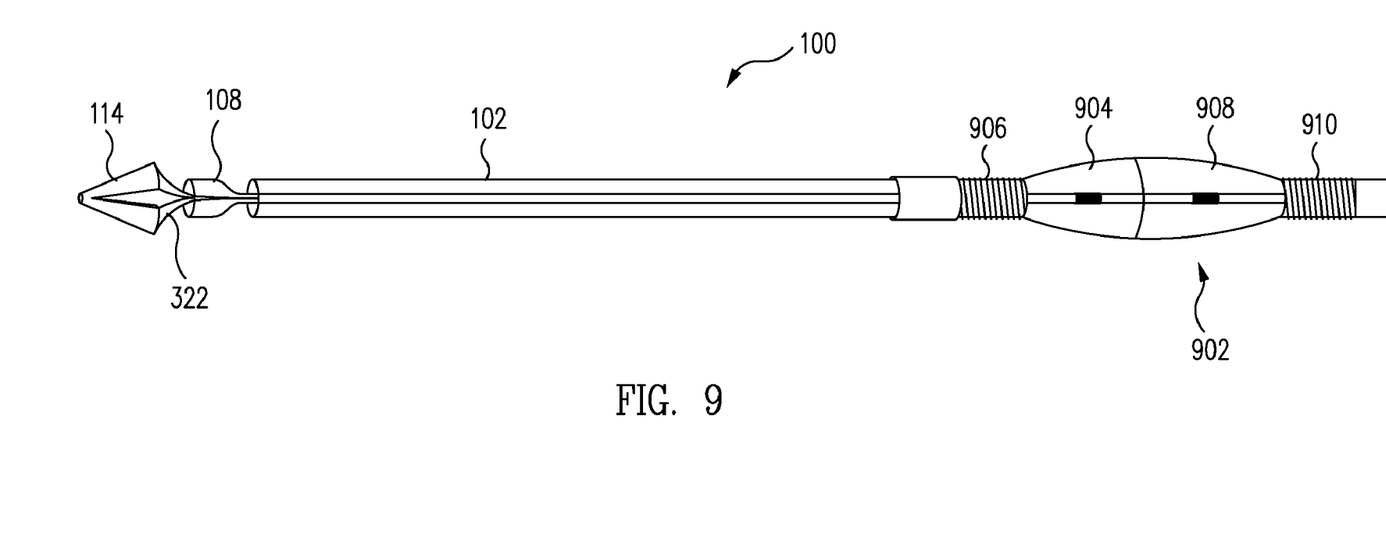
FIG. 9 is a schematic side view of the expandable tip stent-graft delivery system of FIG. 1 illustrating a handle of the expandable tip stent-graft delivery system.

FIG. 9 is a schematic side view of expandable tip stent-graft delivery system 100 of FIG. 1 illustrating a handle 902 of expandable tip stent-graft delivery system 100. Handle 902 includes a forward grip 904, forward screw threads 906, a rear grip 908, and rear threads 910. Sheath 102 is connected to rear grip 908 in a manner that allows rear grip 908 to be rotated without rotation of sheath 102 using any one of a number of techniques well known to those of skill in the art. Runners 322 are connected to forward grip 904 in a manner that allows forward grip 904 to be rotated without rotation of runners 322 also using any one of a number of techniques well known to those of skill in the art.

Forward grip 904 is threadably engaged with forward screw threads 906. Forward grip 904 is rotated in a first direction on forward screw threads 906 to advance forward grip 904 and thus runners 322 to deployed expandable tip 114 as discussed above. Conversely, forward grip 904 is rotated in a second direction on forward screw threads 906 opposite the first direction to retract forward grip 904 and thus runners 322 to collapse expandable tip 114 as discussed above. Generally, rotation of forward grip 904 causes axial translation of forward grip 904 and runners 322.

Rear grip 908 is threadably engaged with rear screw threads 910. Rear grip 908 is rotated in the second direction on rear screw threads 910 to retracted rear grip 908 and thus sheath 102 to deployed stent-graft 106 (not illustrated in FIG. 9, see FIGS. 7-8 for example) as discussed above. Generally, rotation of rear grip 908 causes axial translation of rear grip 908 and sheath 102. Although handle 902 is set forth, an expandable tip stent-graft delivery system similar to expandable tip stent-graft delivery system 100 can be formed using any one of a number of different handles for axial translation of runners 322 and sheath 102. For example, forward grip 904 and/or rear grip 908 can include buttons that allow the grips to slide and or lock in position. In another example, screw gears are used to cause axial translation of runners 322 and/or sheath 102.

Figure 10:
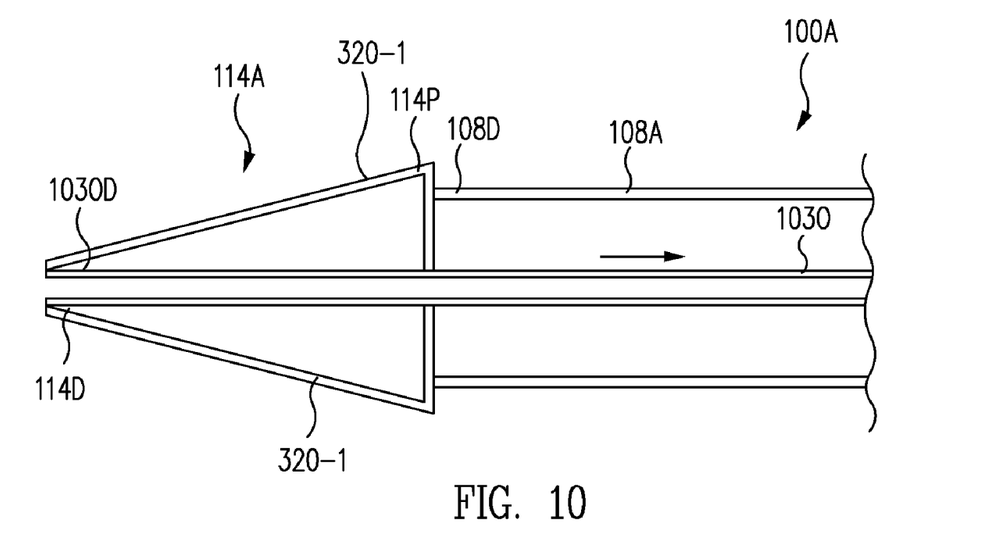
FIGS. 10 and 11 are schematic cross-sectional views of an expandable tip stent-graft delivery system at various stages during deployment of an expandable tip in accordance with another embodiment.
Figure 11:
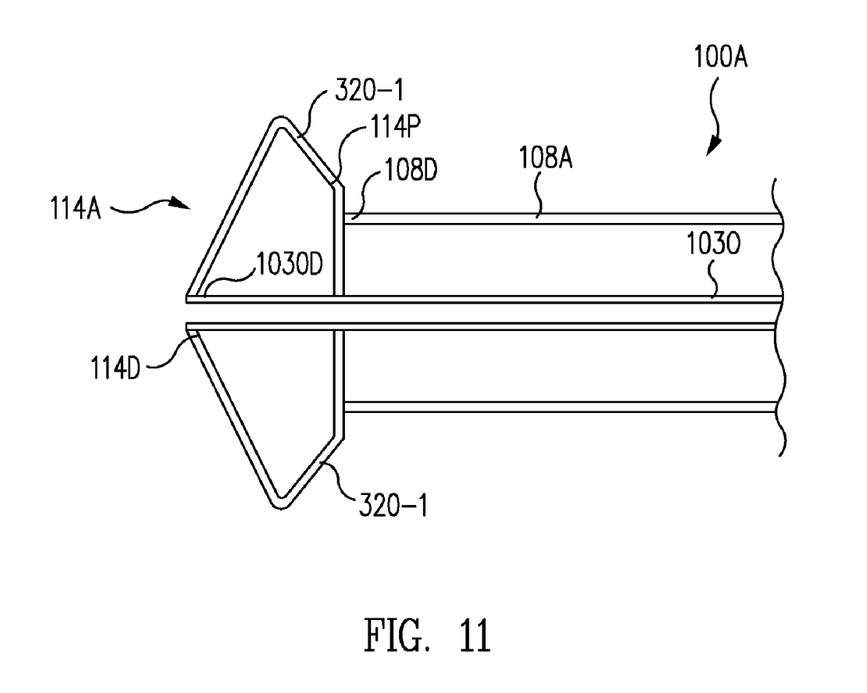

FIGS. 10 and 11 are schematic cross-sectional views of an expandable tip stent-graft delivery system 100A at various stages during deployment of an expandable tip 114A in accordance with another embodiment. Expandable tip stent-graft delivery system 100A of FIGS. 10 and 11 is similar to expandable tip stent-graft delivery system 100 of FIG. 1 and includes a sheath and a stent-graft similar to sheath 102 and stent-graft 106 (FIG. 1), which are not illustrated in FIGS. 10 and 11 for clarity of presentation.

Referring now to FIG. 10, expandable tip 114A is mounted on a distal end 108D of an inner member 108A. Expandable tip 114A includes tip petals 320-1.

Expandable tip stent-graft delivery system 100A further includes a guide wire member 1030, e.g., a tube, defining a guide wire lumen therein. A distal end 1030D of guide wire member 1030 is connected to distal end 114D of expandable tip 114A.

Retraction of guide wire member 1030 causes retraction of distal end 114D of expandable tip 114A. However, as proximal end 114P of expandable tip 114A is mounted to inner member 108A, proximal end 114P is held stationery during retraction of distal end 114D.

Accordingly, retraction of guide wire member 1030 compresses expandable tip 114A and thus tip petals 320-1 longitudinally between proximal end 114P and distal end 114D of expandable tip 114A. This causes tip petals 320-1 to bend radially outwards increasing the overall diameter of expandable tip 114A as illustrated in FIG. 11. In one embodiment, expandable tip 114A is heat set to insure longitudinal compression of expandable tip 114A causes tip petals 320-1 to bend outwards.

Conversely, advancement of guide wire member 1030 causes tension in (stretches) expandable tip 114A and thus tip petals 320-1 longitudinally between proximal end 114P and distal end 114D of expandable tip 114A. This causes tip petals 320-1 to collapse radially inwards returning expandable tip 114A to the stage illustrated in FIG. 10.

In one example, expandable tip stent-graft delivery system 100 of FIG. 1 includes a guide wire member similar to guide wire member 1030 of FIGS. 10 and 11. This guide wire member holds distal end 114D of expandable tip 114 stationery during advancement and retraction of runners 322.

The drawings and the forgoing description gave examples of embodiments according to the present invention. Numerous variations, whether explicitly given in the specification or not, such as differences in structure, dimension, and use of material, are possible.

What is claimed is:

1. An expandable tip stent-graft delivery system comprising:
  an expandable tip member comprising:
    a plurality of splines comprising long narrow non-hollow strips of material, said splines comprising:
    tip petals;
    runners; and
    elbows connecting said tip petals to said runners, wherein said elbows have a smooth outer edge between said tip petals and said runners, said tip petals collectively forming an expandable tip of said expandable tip member;
  an inner member defining a lumen therein through which said runners extend;
  wherein said runners are coupled to said expandable tip through said inner member;
  a sheath defining a lumen therein through which said inner member extends; and
  a stent-graft radially constrained in an annular space between said sheath and said inner member wherein said expandable tip is configured to be collapsible by retracting said runners through said inner member and configured to be expandable through advancing said runners through said inner member.

2. The expandable tip stent-graft delivery system of claim 1 wherein said material is selected from the group consisting of nitinol, stainless steel, and polymer.

3. The expandable tip stent-graft delivery system of claim 1 wherein distal ends of said splines are connected to one another to form a distal end of said expandable tip.

4. The expandable tip stent-graft delivery system of claim 3 wherein said distal end of said expandable tip comprises a guide wire opening.

5. The expandable tip stent-graft delivery system of claim 1 wherein a first spline of said plurality of splines comprises a first tip petal of said plurality of tip petals, a first runner of said plurality of runners, and a first elbow of said plurality of elbows, said first runner being connected to said first tip petal by said first elbow.

6. The expandable tip stent-graft delivery system of claim 1 wherein said tip petals extend proximally from a distal end of said expandable tip to said elbows.

7. The expandable tip stent-graft delivery system of claim 6 further comprising a handle, said runners extending proximally from said elbows to said handle.

8. The expandable tip stent-graft delivery system of claim 7 wherein said handle comprises a grip and screw threads, said grip being coupled to said runners and threadably engaged with said screw threads.

9. The expandable tip stent-graft delivery system of claim 8 wherein rotation of said grip causes axial translation of said runners.

10. The expandable tip stent-graft delivery system of claim 7, wherein said handle further comprises a grip and screw threads, said grip being coupled to said sheath and threadably engaged with said screw threads.

11. The expandable tip stent-graft delivery system of claim 10 wherein rotation of said grip causes axial translation of said sheath.

12. The expandable tip stent-graft delivery system of claim 1 wherein said expandable tip is in its collapsed configuration, said expandable tip comprising a tapered outer surface.

13. The expandable tip stent-graft delivery system of claim 12 wherein said tip petals have a minimum width at a distal end of said expandable tip and gradually increase in width proximally to have a maximum width at said elbows.

14. The expandable tip stent-graft delivery system of claim 12 wherein said tip petals are in contact with one another substantially along an entire length of said tip petals.

15. The expandable tip stent-graft delivery system of claim 1 wherein said runners have a substantially uniform width.

16. The expandable tip stent-graft delivery system of claim 1 wherein said runners have flared ends at distal ends at said runners.

17. The expandable tip stent-graft delivery system of claim 1 wherein said expandable tip is seated on a distal end of said inner member.

18. The expandable tip stent-graft delivery system of claim 17 wherein said inner member radially constrains said expandable tip when said expandable tip is in its collapsed configuration.

19. The expandable tip stent-graft delivery system of 18 wherein said expandable tip is released from said inner member when said expandable tip is in its relaxed configuration.

20. The expandable tip stent-graft delivery system of claim 19 wherein said expandable tip has a greater outer diameter in its relaxed configuration than in its collapsed configuration.

21. The expandable tip stent-graft delivery system of claim 1 wherein said elbows are hinged between said tip petals and said runners.

22. A method of deploying a stent-graft in a vessel with an expandable tip stent-graft, delivery system, said method comprising:
  deploying an expandable tip of said expandable tip stent-graft delivery system to center a distal end of a catheter containing said stent-graft in said vessel comprising advancing runners coupled to said expandable tip through an inner member of said expandable tip stent-graft delivery system, wherein said advancing runners advances the entire expandable tip relative to said inner member, said stent-graft being radially constrained in an annular space between a sheath and said inner member of said expandable tip stent-graft delivery system;
  subsequent to said deploying, retracting said sheath of said expandable tip stent-graft delivery system to expose said stent-graft, wherein said stent-graft self-expands into said vessel upon said retracting; and
  collapsing said expandable tip, wherein said collapsing said expandable tip comprises retracting said runners through said inner member.

23. The method of claim 22 wherein said inner member radially constrains said expandable tip prior to said deploying an expandable tip, wherein said advancing runners causes said inner member to release said expandable tip.

24. The method of claim 23 wherein said expandable tip self-expands upon said release.

* * * * *